United States Patent
Unbehaun et al.

(10) Patent No.: US 10,519,354 B2
(45) Date of Patent: Dec. 31, 2019

(54) POROUS OIL BINDER AND METHOD FOR THE PRODUCTION THEREOF

(71) Applicants: TECHNISCHE UNIVERSITAT DRESDEN, Dresden (DE); UNIVERSITAT LEIPZIG, Leipzig (DE)

(72) Inventors: Holger Unbehaun, Dresden (DE); Soren Tech, Dresden (DE); Swetlana Konig, Leipzig (DE); Elena Safonova, Leipzig (DE); Andre Wagenfuhr, Dresden (DE); Christian Wilhelm, Markleeberg (DE)

(73) Assignees: Technische Universitaet Dresden, Dresden (DE); Universitaet Leipzig, Leipzig (DE)

( * ) Notice: Subject to any disclaimer, the term of this patent is extended or adjusted under 35 U.S.C. 154(b) by 731 days.

(21) Appl. No.: 14/915,198

(22) PCT Filed: Aug. 27, 2014

(86) PCT No.: PCT/EP2014/068168
§ 371 (c)(1),
(2) Date: Feb. 26, 2016

(87) PCT Pub. No.: WO2015/028506
PCT Pub. Date: Mar. 5, 2015

(65) Prior Publication Data
US 2016/0200602 A1 Jul. 14, 2016

(30) Foreign Application Priority Data
Aug. 27, 2013 (DE) .......... 10 2013 217 016

(51) Int. Cl.
| | | |
|---|---|---|
| C02F 1/68 | (2006.01) | |
| C09K 3/32 | (2006.01) | |
| C02F 3/34 | (2006.01) | |
| C12N 11/02 | (2006.01) | |
| B01J 20/24 | (2006.01) | |
| B01J 20/28 | (2006.01) | |
| E02B 15/10 | (2006.01) | |
| D04H 1/732 | (2012.01) | |
| D04H 1/425 | (2012.01) | |
| C02F 101/32 | (2006.01) | |
| C02F 103/00 | (2006.01) | |
| C02F 1/28 | (2006.01) | |

(52) U.S. Cl.
CPC ............ *C09K 3/32* (2013.01); *B01J 20/24* (2013.01); *B01J 20/28011* (2013.01); *B01J 20/28038* (2013.01); *B01J 20/28054* (2013.01); *C02F 3/348* (2013.01); *C12N 11/02* (2013.01); *D04H 1/425* (2013.01); *D04H 1/732* (2013.01); *E02B 15/101* (2013.01); *B01J 2220/4831* (2013.01); *C02F 1/285* (2013.01); *C02F 1/681* (2013.01); *C02F 2101/32* (2013.01); *C02F 2103/001* (2013.01); *C02F 2103/007* (2013.01); *Y02A 20/204* (2018.01)

(58) Field of Classification Search
CPC ........... B01J 20/24; B01J 20/28011; B01J 20/28054; C02F 1/681; C02F 3/348; C12N 11/02; C12N 9/2494; C12N 9/2491; C12N 9/0008; C12P 19/02; C12P 19/14; C12P 2203/00; C12P 7/10; C12Y 302/01078; C12Y 302/01025; C10G 1/002; C10G 1/06; C10G 2300/1014; C10G 2400/02; C10G 2400/04; D21H 11/00; D21H 11/18; D21H 27/002; Y02P 30/20; Y10T 428/249966; B02C 7/12; D21D 1/30; D21D 1/306; G01N 2333/924; Y02E 50/16
USPC .......................... 435/29, 39, 42, 177, 262.5
IPC ............... C02F 3/34; C09K 3/32; C12N 11/02
See application file for complete search history.

(56) References Cited

U.S. PATENT DOCUMENTS

| | | | |
|---|---|---|---|
| 5,110,785 A * | 5/1992 | Reed .................. | B01J 20/24 |
| | | | 502/404 |
| 7,655,149 B1 | 2/2010 | Shaffer et al. | |
| 2013/0177686 A1 | 7/2013 | Schleppinghoff et al. | |

FOREIGN PATENT DOCUMENTS

| | | | |
|---|---|---|---|
| AT | 347 362 B | 12/1978 | |
| DE | 2 212 605 A1 | 11/1972 | |
| DE | 2 301 176 A | 7/1973 | |
| DE | 693 03 756 T2 | 12/1996 | |
| DE | 69303756 T2 * | 12/1996 | .......... E02B 15/101 |
| DE | 196 28 751 A1 | 1/1998 | |
| DE | 19954643 A1 * | 6/2001 | ........ B01D 17/0202 |
| DE | 100 39 875 A1 | 3/2002 | |

(Continued)

OTHER PUBLICATIONS

DE 19954643 A1, English Language Translation.*

(Continued)

*Primary Examiner* — Lisa J Hobbs
(74) *Attorney, Agent, or Firm* — FisherBroyles, LLP; Andrew K. Gonsalves, Esq.

(57) ABSTRACT

The invention relates to a hydrophobed porous oil binder in the form of a nonwoven fabric composed of lignocellulose-containing raw materials having a biologically functionalized surface for removing mineral-oil-based contaminants in seas, rivers, inland waters, and stormwater basins or wastewater treatment plants, wherein the density of the oil binder is 10 to 900 kg/m$^3$, the oil binder is 1 to 25 mm thick, the broad surface of the oil binder has a dimension of 9 to 200 cm$^2$, the porosity of the oil binder is 30 to 96%, measured with respect to the total fraction of the oil binder, and the flexural strength of the oil binder is at least 1.5 N/mm$^2$.

10 Claims, No Drawings

(56) References Cited

FOREIGN PATENT DOCUMENTS

| | | |
|---|---|---|
| DE | 101 11 638 A1 | 9/2002 |
| DE | 102 44 122 C1 | 10/2003 |
| DE | 102 48 539 A1 | 5/2004 |
| DE | 103 03 198 A1 | 7/2004 |
| DE | 103 34 967 A1 | 3/2005 |
| DE | 20 2010 003 238 U1 | 9/2011 |
| JP | S5276287 A | 6/1977 |

OTHER PUBLICATIONS

DE 69303756 T2, English Language Translation.*

2012.Tip 8, Use of Sorbent Materials in Oil Spill Response. Technical Information Paper, The International Tanker Owners Pollution Federation Limited (i.e., ITOPF),13 Pages.*

Cerniglia et al 1980. Oxidation of Naphthalene by Cyanobacteria and Microalgae. Journal of General Microbiology, vol. 116, pp. 495-500).*

Safonova et al., (2004) "Biotreatment of industrial wastewater by selected algal-bacterial consortia," Engineering in Life Sciences, 4:347-353.

Coulibaly et al., (2003) "Utilization of fungi for biotreatment of raw wastewaters," Afr. J. Biotechnol. 2(12):620-630.

Machate et al., (1997) "Degradation of phenanthrene and hydraulic characteristics in a constructed wetland," Wat. Res. 31(3):554-560.

Delille et al., (1998) "Effectiveness of bioremediation for oil-polluted Antarctic seawater," Polar Biol. 19:237-241.

Stephen et al., (1999) "Developments in terrestrial bacterial remediation of metals," Curr. Opin. Biotechnol. 10(3):230-233.

Delille et al., (2000) "Field observations on the variability of crude oil impact in indigenous hydrocarbon-degrading bacteria from sub-Antarctic intertidal sediments," Mar Environ Res 49:403-417.

Koppe et al., (2003) "SORBMOP—Clean-Up Technology for Oil Spills,". Proc. 6th Conference on Coastal and Port E, COPEDEC VI, Colombo, Sri Lanka.

Oswald, W. J., (1995) "Ponds in the twenty-first century," Wat. Sci Tech 31(12):1-8.

Siron et al., (1995) "Environmental factors influencing the biodegradation of petroleum hydrocarbons in cold seawater," Arch Environ Contam Toxicol 28:406-416.

Safonova et al., (1999) "The interaction of algae with alcanotrophic bacteria in black oil decomposition," Resources, Conservation and Recycling 27:193-201.

German Patent & Trade Mark Office, German Office Action issued in German Counterpart Application No. DE 10 2013 217 016.5, dated Apr. 10, 2014.

German Patent & Trade Mark Office, German Office Action issued in German Counterpart Application No. DE 10 2013 217 016.5, dated Jul. 15, 2016.

* cited by examiner

POROUS OIL BINDER AND METHOD FOR THE PRODUCTION THEREOF

CROSS REFERENCE TO RELATED APPLICATIONS

This application is a U.S. National Phase filing under 35 U.S.C. § 371 of International Application No. PCT/EP2014/068168, filed Aug. 27, 2014, and published as WO 2015/028506-A1 on Mar. 5, 2015, which claims priority to German Patent Application No. DE 10 2013 217 016.5, filed Aug. 27, 2013, the entire disclosures of which are hereby incorporated herein by reference.

FIELD OF THE INVENTION

The invention relates to porous, buoyant, biologically degradable oil binders with biologically functionalized surfaces for the accelerated degradation or removal of mineral oil-based contamination in seas, rivers, inland waters as well as storage reservoirs or wastewater treatment plants, and to a method for the production of these porous, fully buoyant oil binders for the accelerated degradation or removal of oil contamination from the water surface in bodies of water.

BACKGROUND OF THE INVENTION

Oil is a complex mixture of organic compounds: aromatics, alkenes, alkanes, paraffins, naphthenes as well as isolated elements such as nitrogen, oxygen, sulphur, sodium, nickel, iron, vanadium and others. It is primarily transported as crude oil. However, fractions therefrom such as diesel oil, heating oil and bunker oil are also frequently transported by sea. The problems which arise when combating the threat of spilled oil are primarily due to the speed at which the oil slicks spread out and become isolated, and the mixing of oil and water.

Accidents during the production and transportation of oil or mineral oil products at sea and the processing of oil give rise to more and more contamination of sea and coastal regions with oil. The viscous oil sludge can only very slowly be degraded naturally in the water and on land.

In addition to ecological damage, when oil spills at sea, economic damage also occurs in the form of clean-up costs, production losses, falls in income in the fishing and tourism industries as well as prosecution costs. The prompt and inexpensive removal of contamination by oil in marine environments is thus an important matter.

Currently, various systems for removing marine oil contamination have been proposed and are employed; their effectivity depends on multiple factors. In the first place these are the characteristics of the oil, weather conditions, water temperature, salinity, water depth and accessibility of the marine environment with technical equipment, as well as the removal to sensitive ecosystems or coastal areas which are used by people. The following methods for removing oil contamination at sea can in principle be used:

- collecting the oil using physico-mechanical methods
- using chemical agents to change the characteristics of the oil and to distribute the oil in the body of water (dispersion)
- using fertilizers to support natural biodegradation
- heat treating the spilled oil
- cleaning the coastline using physico-mechanical methods The current technologies for recovering oil at sea are of limited application and effectiveness under inclement weather, swell and current conditions. In particular, removing oil in shallow marine regions and in regions close to the coast is a further problem because of the deep draught of many oil recovery vessels and by the comparatively short time available. Frequently, shallow water regions close to coasts are distinguished by an augmented ecological sensitivity. The use of thermal or chemical methods is not possible in these regions.

The preferred system for oil recovery in coastal regions consists of special vessels, mobile counter-measures such as oil barriers, lighterage systems, high pressure cleaners, skimmers etc., as well as monitoring from the air to detect and observe oil contamination. The special vessels used in coastal waters have special equipment for isolating and skimming oil from the water surface and for recovering the oil into tanks on the ships.

One of the most important points when controlling oil spills is the prompt use of effective counter-measures after an incident, in order to prevent the contamination from spreading out over a wide area and thus of endangering large habitats as well as coastal regions which are used for tourism and industry. In addition, it is frequently only prompt reaction that can result in extensive removal of the contamination, since after spilling over the water surface, the properties of the oil change rapidly. Evaporation of the light components means that after a short time, the oil forms a sticky, solid slick which can remain buoyant in water over a long period or can form clumps which sink to the bottom of the sea. The viscous oil sludge can only slowly be degraded by natural biodegradation on land or at sea.

With the systems which are in global use, rapid and ecologically meaningful intervention is not possible in many cases of incidents. The problems occur in particular because of inclement meteorological and hydrological conditions, both in shallow water regions and in areas near the coast. Frequently, it takes several days just for ships carrying the oil spill recovery systems to travel from their home base to the scene of the incident. Then there are often more delays due to inclement weather conditions, since the deployment of contemporary cleaning systems requires the sea to be relatively calm. In this manner, clean-up measures often can only be begun days or even weeks after the oil has been spilled. In summary, it can be seen that existing systems for cleaning oil contamination at sea can in most practical cases only achieve unsatisfactory clean-up rates. Even under optimal conditions, currently available mechanical clean-up systems can only reach clean-up rates of about 15%, while rates below 10% are the norm.

Oil binders are used to adsorb/absorb spilled oil. In this manner, damage or danger to people and to the environment can be reduced. The spilled oil can also be picked up more easily and disposed of when in combination with oil binders. The use of oleophilic, hydrophobic binder materials as a counter-measure for oil damage is not new. Binders can be categorized into active and passive binders. In the active category, the binders are introduced into the oil contamination, for example from a ship, and then directly removed from the body of water (skimmers, oil barriers, continuous fibre bundles). In these methods, the binders are in constant contact with the ship or another means of transport.

With passive counter-measures, the binder is introduced into the contamination from the air or from the ship as a granulate, nonwoven material or floating barrier, released there and only removed from the body of water again after a period of time. When oil binders are used passively in bodies of water, the binders are buoyant with and without being wetted by the oil and configured such that as far as possible, they still float when recovered.

Many different mineral and organic materials are available on the market for use as oil binders. These are set down in the "Liste der geprüften Ölbindemittel Typ I, II, III and IV" [List of approved Type I, II, III and IV oil binders] published in April 2013 by the Approved Oil and Chemical Binder Producer Consortium (GÖC e.V.).

Tests on the use of passive binders in a marine environment have shown that the take-up of deployed binders is a problem which has not yet been solved in a satisfactory manner, and thus the use of scattered and nonwoven materials to control oil incidents at sea has been avoided (OEBIUS, H. (2002): "Controlling oil spills in water" GMAG Seminar "Binders", Equipment and Means for Controlling Hazards in an Aquatic Environment" (GMAG)).

A problem when using binders which has not been solved is the introduction of other materials into the sea which do not degrade or only degrade slowly. During the degradation process, some toxic substances may be formed. When recovering binders which have been deployed, only a portion of the binder which has been distributed can ever be picked up, which portion depends on the meteorological and hydrodynamic conditions and on the recovery technique employed.

As an example, Koppe et al. (KOPPE, B.; KOHLHASE, S.; SCHULZ-BULL, D.; JÜRGENS, M. W. (2003): "SORBMOP—Clean-Up Technology for Oil Spills". Proc. 6th Conference on Coastal and Port E) describes an oil incident clean-up system in which polymeric binders formed from hydrophobic and oleophilic polyurethane polymer materials with high adsorption rates are used.

The use of buoyant foam elements has also been described in DE 100 39 875 A1. These are deployed by ships or aircraft and are collected and burned with the aid of nets. Deploying oil binder systems which cannot be biologically degraded is, however, not permitted by the authorities in many marine regions and in particular on the Baltic Sea for environmental reasons.

DE 102 48 539 A1 discloses an absorption mat to absorb liquids, preferably oils or similar substances from liquid media or a solid substrate, which is characterized in that between two fluid-permeable textile webs such as a stitch-bonded nonwoven, a needled nonwoven, a woven material, a knit or a composite nonwoven is an intermediate layer formed from a biologically degradable absorption material, wherein the textile webs are connected together by means of seam-like connections and the absorption material is enclosed in a stable manner between the connecting seams by the nonwoven webs.

The absorption material is formed by an organic support material formed from leather in the form of fibres, granulate, pellets or other pourable free-flowing forms impregnated with oil-degrading microorganisms in order to ensure a rapid and complete absorption of oil or oil-containing pollutants and at the same time to ensure degradation of the pollutant absorbed into the mat during deployment and also recovery and storage.

The absorbant textile is preferably provided to prevent oily contamination, to recycle it in many ways and to be rapidly and smoothly transported and deployed at the scene of operation and to be is available in a sufficient quantity and with appropriate dimensions.

The disadvantage with this absorption mat is the comparatively complicated construction of several functional layers, including several textile webs, which mechanically enclose the absorption means in a stable manner and which are bonded together by means of seam-like connections.

DE 102 44 122 C1 discloses an oil binder mat for isolating and/or removing contamination such as fossil oils, synthetic oils, lubricants, fuels, mineral oils, including hydrocarbons or hydrocarbon mixtures, preferably on the surface of water or the surfaces of solid ground formed by organic binders with a flat envelope.

In this regard, the hydrophobic binder is disposed in the flexible textile envelope which is permeable to hydrophobic liquids formed from cotton material, wovens, knits, nonwovens and other materials.

The flat envelope contains a silicone-based coating which has been hydrophobized and is impermeable to hydrophilic liquids, water-soluble substances and the binder but permeable to lipophilic substances.

The advantages of the oil binder arise from the particular relationship of the mat surface to the binder. The weight ratio of binder to envelope is 5:1 to 25:1, wherein the binder has a grain size of up to 4.3 mm, an apparent density of 0.2-0.7 $g/cm^3$ with an absorption capacity of 0.15-0.75 L of heating oil/L of binder. The binder contains granulated brown coal and the basis weight of the envelope is also 250 to 350 $g/m^3$. Particularly preferably, a mixture of a selected brown coal fraction and unadulterated tree bark or materials such as sawdust, peat and plant fibres is used. Admixing the bark means that the basis weight is reduced and the combustion temperature is dropped.

The mats, in particular the binders contained therein, may also be coated with microorganisms. These organisms are from the genuses *Pseudomonas, Bacillus, Mesorhizobium* and *Pseudaminobacter*.

It has been shown that as regards oil uptake, the binders only reach their full effectiveness because they are enclosed in the water-repellent/oil permeable envelope, since upon earlier contact with water, which often occurs when deployed, the absorption capacity of the binder (for example brown coal) then reduces substantially for oily liquids.

Furthermore, without the textile cover, the buoyancy does not last for long. The buoyancy of the mats can be additionally increased by attaching buoyancy aids produced from wood, polystyrene or the like without departing from the scope of the invention.

Problem-free and controlled deployment, and above all recovery, even under poor weather conditions, is also only possible because of the textile envelope. The oil binder mats are thus transported by ship to the scene of the oil spill and then deployed onto the surface of the water (for example by rolling out or application).

The disadvantage with these oil binder mats is the comparatively complicated construction from a textile envelope which is prepared with an acidic, oil and water-resistant polyester yarn and also encloses the organic binder material, and additionally can be provided with buoyancy aids. In addition, the buoyancy of the oil binder mat is only possible because the textile cover used has been hydrophobized. Furthermore, the oil binder mats can only be transported to and recovered from the scene of operations by ship.

DE 20 2010 003 238 U1 discloses a device for absorption and/or isolation of liquids which are not miscible with water such as fossil oils, synthetic oils, lubricants, fuels, mineral oils, hydrocarbons or hydrocarbon mixtures, preferably on the surface of water or the surfaces of solid ground.

In this regard, a binder containing brown coal is introduced into an envelope formed from a natural substance or a synthetic substance, in particular wool, cotton, polyester, polyethylene, polypropylene or other polyolefins. The envelope has a hydrophobic surface modification, in particular in the form of a siliconization which is applied by immersion, brushing or spraying onto the outer or each individual layer of the envelope, whereupon they are impermeable to hydrophilic liquids and the binder. The envelope may be generally flat or in the shape of a roll and have a circumferential edge reinforcement, in particular in the form of a woven strip. An example of a flat embodiment is the formation of cushions or mats. In addition, the envelope has at least two interconnected or separate chambers, preferably arranged as cassettes or in parallel, which are filled with binder.

The binder is at least 50% by weight, preferably at least 80% by weight, particularly preferably completely formed by brown coal coke. If brown coal coke is exclusively used as the binder, oil absorption from water in amounts from 0.3 to nearly 1 litre of oil per litre of binder may be obtained. Furthermore, the binder may contain other components such as brown coal, charcoal, activated charcoal, granulated tree bark, granulated wood or wood chips, peat, plant fibres and/or mineral binders such as alumina or other silicate materials such as fumed silica or precipitated silica. The device does not contain any additional flotation or buoyancy devices.

The disadvantage with this device is the comparatively complicated construction from an envelope, preferably formed by two or three layers, which is provided with chambers.

U.S. Pat. No. 7,655,149 B1 discloses oil-absorbing kenaf balls, wherein the kenaf fibres have been entangled in order to obtain balls which have been shown to be extremely useful in the absorption of oil and other organic liquids on land or water.

The product can in this regard adopt many forms such as spherical, longitudinal, ball-shaped, conical, cylindrical etc. For some applications the kenaf balls may be connected together in order to obtain a mat-like, rolled, blanket-like, bag-like or rope-like arrangement. In addition, they can be woven into a cover or cloth in order to be able to clean small oil-contaminated regions. The kenaf balls may also be used to remove oils from the surface of water. They may, for example, absorb crude oil, engine oil, light oil, transmission oil or even plant oils. The kenaf balls are water-repellent and are also buoyant for a long period on the water. They have a much greater affinity for absorbing oil than water. The kenaf balls can absorb oil in a quantity of more than 1000% of its own weight, in some cases more than 1800% of its own weight. The balls have a density in the range 0.02 $g/cm^3$ to approximately 0.15 $g/cm^3$ and a mass of 0.2 g to 10 g.

The disadvantage with oil-absorbing kenaf balls is that it does not appear to be possible to deploy them with the aid of an aircraft on the surface of the water when the weather in rough because of their low mass. In addition, the spherical shape of the kenaf balls is somewhat disadvantageous when absorbing thin slicks of oil from the water surface, since only a small part of the spherical surface is wetted by the oil. Trapping them in some sort of net would also require a very small mesh size.

DE 103 34 967 A1 discloses a buoyant oil absorber to remove oil-containing contamination on water surfaces, in which an absorbent formed from loose buoyant wood fibres in the form of chips, sawdust, chips or fibres. The oil binding capability is still further improved when, in accordance with a preferred embodiment of the oil absorber, the wood fibres contain comminuted stalks of buoyant renewable raw materials such as *Juncus effusus* (common rush), *Scirpus Lacustris* (common clubrush) or other plants which have air pockets in the intercellular voids of the aerenchyma, as a filler.

The absorption material is formed into a rope and surrounded by a net-like sheath formed from a large mesh structure of fibres, strips of foil or the like. Parallel to the longitudinal direction of the rope is a tensioning element which consists of a buoyant water-repellent fibrous material. That invention is characterized in that a plurality of buoyant ropes at the rope ends which are completely surrounded by the net-like sheath and contain no absorption material, are connected together in the longitudinal direction. The flexible ropes may also be joined together like a mat; the size and thickness of the material can be varied and is appropriate to the purpose.

The disadvantage with that buoyant oil absorber is the comparatively complicated construction, wherein the buoyant oil absorber consists of a net-like sheath which contains the absorbent and is formed into a rope which contains a tensioning element to connect the ropes.

DE 103 03 198 A1 discloses a method for absorbing oil from water. Using hydrophobic means packed in jute, filter fleece, nets or other permeable fabrics, oil which is floating on the water is absorbed. The elements may be produced in the form of bags, tubes or mats in any required size, width and length. The slightly hydrophobic material consists of insulating mats or granulates and is impregnated with liquid silicone, siloxane or other hydrophobic agents. They can be dragged across the water in any swell conditions and from any type or size of ship.

The disadvantage with this method is the comparatively complicated construction, wherein the hydrophobic insulating mats or the granulate initially has to be packed into another material and they have to be towed by ships.

DE 101 11 638 A1 discloses an agent and a method for absorbing chemicals, in particular layers of oil floating on the surface of water.

It proposes a binder for absorbing chemicals, in particular layers of oil floating on the surface of water, which consists of a fibrous material which is felted or woven, wherein a mat-like article is produced from the felted or woven fibrous material.

The fibrous material is preferably a natural material which has a high carbon content. Preferably, xylitol is used as the fibrous material, since it is an environmentally friendly natural substance which is obtained when upgrading and processing brown coal. Instead of xylitol, natural fibres may also be used as the fibrous material, preferably natural fibres which are selected from the group consisting of hemp, rape straw, wood fibres, reeds, maize plants and flax. The felted or woven fibres are advantageously dried and/or coked. The mat-like articles obtained are deployed onto the chemicals to be absorbed and then removed again after the chemicals have been bound into the mat-like article.

The disadvantage with this binder for absorbing chemicals is that the fibrous material is felted or woven and after being absorbed, and the binder has to be removed again from the scene of operations.

DE 196 28 751 A1 discloses a buoyant material and its production which is capable of absorbing oils and fats floating on the surface of water. In particular, it is provided for absorbing heavy and light mineral oils, fossil oils, animal and plant oils and fats as well as vehicle fuel.

The buoyant material consists of comminuted and defibrated plant or biologically-derived highly buoyant fibres with a fibre length of ≤15 mm, preferably 1-5 mm, which are coated with a stable hydrophobic protective film of montan resin.

Suitable fibrous materials are all highly buoyant substances of plant or biologically-derived nature such as, for example, wood chips, selected straw or reed chips as well as purified brown coal xylitol. The comminuted chips and fibres are initially saturated with water and then coated with a stable hydrophilic film. Next, water from the pores of the fibres is removed once again by gentle drying. By means of a drying process, the hydrophobic protective sheath is not destroyed but rather the protective film is distributed further due to the heating and the surface of the fibres is rendered completely hydrophobic.

This is ensured because montan resin with particularly good adhesive properties and advantageous distribution capabilities is used on the fibre surface before and during drying. The good distribution capability is characterized by the formation of a thin protective film without penetrating deeply into the pores of the support material. In addition, it was observed that montan resin, because of its chemical composition, is a particularly good binding agent for oils and fats onto the described fibres, for example onto wood chips. In order to securely bind the montan resin to the fibres and for its oil and fat-collecting action, according to DE 196 28 751 A1, its bifunctional character which is determined by the presence of both hydrophilic and hydrophobic functional molecular groups, is of vital importance. It is known that it is not possible to coat materials saturated with water with hot liquid montan resin, which has a melting range of 75° C. to 85° C., because hot liquid products such as oils, fats, waxes and resins do not adhere to moist surfaces and in addition, difficult mixing conditions arise because of the build-up of water vapour. According to DE 196 28 751 A1, then, a hydrophobizing material has to be found which allows for stable binding to the moist surface of the support material far below its melting temperature and which also ensures that the protective layer remains in place when it has dried. The fibrous material conditioned with montan resin has a moisture content of approximately 5% to 20%.

The disadvantage with this floating material is that rendering the fibrous surface hydrophobic using montan resin is limited. Furthermore, only loose fibres and/or chips are used, which are difficult to remove from the water later. In addition, the agglomerated structures formed after absorbing oil have to be collected, for example, by skimming or combing before they sink to the bottom.

DE 2 212 605 A1 discloses a method for removing oily contamination such as oil spots from bodies of water, using finely divided wood pulp which has been hydrophobized. In this regard, the wood pulp is hydrophobized by treatment with a synthetic or natural sizing agent such as resin size, a wax emulsion, an emulsion of a dimeric alkylketene, a stearic acid anhydride emulsion or a different natural or synthetic sizing agent, and when resin size is used, alum, aluminium chloride, sodium aluminate, a water-soluble alumina salt or a chromium, alkaline-earth, iron or manganese salt is also used. The flakes act to remove oil from the surface of the water and are then compressed into briquettes.

The disadvantage here is the low density and strength of the flaky form of the binder, which means that it cannot be deployed from the air and cannot be recovered using nets.

AT 347 362 B discloses an agent based on cellulose or wood fibres to absorb and/or bind environmentally dangerous liquids in particular, and a method for its production. In this regard, the raw material is constituted by rejects from sorting and cleaning units and/or sludge from wastewater plants from paper and/or cell production and if appropriate, "tree" material separated out as waste from cellulose production, wherein these waste materials may if appropriate be hydrophobized with a hydrophobizing agent. These are used in the granulated or pelletized form as an oil binder.

The disadvantage with this binder is the use of the rejects from the paper industry, which contains large proportions of plastics and metal and only a small proportion of wood fibre. In addition, the pelletized form of the binder is a disadvantage.

JP S5276287 A discloses an oil binder material consisting of wood chips which have been impregnated with a paraffin wax emulsion, a zirconium salt and a phenolic resin.

The disadvantage here is the use of oil binders in the form of wood chips.

The biological degradation of many hydrocarbons contained in mineral oils by microorganisms has been described in many types of terrestrial and marine ecosystems, as well as in the soil and in seawater (DELILLE D., BASSÈRES A., DESSOMMESS A. (1998): Effectiveness of bioremediation for oil-polluted Antarctic seawater. Polar Biol 19:237-241; DELILLE D., DELILLE B. (2000): Field observations on the variability of crude oil impact in indigenous hydrocarbon-degrading bacteria from sub-Antarctic intertidal sediments. Mar Environ Res 49:403-417; SIRON R., PELLETIER E., BROCHU C. (1995): Environmental factors influencing the biodegradation of petroleum hydrocarbons in cold seawater. Arch Environ Contam Toxicol 28:406-416).

In the bioremediation of contaminated ecosystems, bacteria are preferred (STEPHEN J. R., MACNAUGHTON S. J. (1999): "Developments in terrestrial bacterial remediation of metals". Curr. Opin. Biotechnol. 10 (3), 230-233) and Pilze (COULIBALY L., GOURENE G., AGATHOS N. S. (2003): "Utilization of fungi for biotreatment of raw wastewaters". Afr. J. Biotechnol. 2 (12), 620-630). In the last century, interest in bioremediation using plants, i.e. phytoremediation, has grown substantially (MACHATE T., NOLL H., BEHRENS H., A. KETTRUP A. (1997): "Degradation of phenanthrene and hydraulic characteristics in a constructed wetland". Wat. Res. 31 (3), 554-560). Algae are often used to clean up agricultural and communal bodies of water (OSWALD, W. J. (1995), Ponds in the twenty-first century. Wat. Sci Tech, vol. 31, No. 12, pp. 1-8). These organisms have not yet been employed to remove oils and polycyclic hydrocarbons.

It is known that associations consisting of different organisms can preferably be used for bioremediation, since there are practically no organisms which are capable of degrading all components of such complicated contamination (OSTWALD, W. J., (1995), Ponds in the twenty-first century. Wat. Sci Tech, vol. 31, No. 12, pp. 1-8).

When used in a stationary situation on land, phototrophic partners such as eukaryotic algae or cyanobacteria in combination with heterotrophic partners such as alkanotrophic bacteria, for example, were investigated in order to clean up industrial wastewater; oil residues were also degraded (SAFONOVA E., KVITKO K. V., IANKEVITCH M. I, SURGKO L. F., AFTI I. A., REISSER W. (2004) Biotreatment of industrial wastewater by selected algal-bacterial consortia//Engineering in Life Sciences, V. 4. P. 347-353). In those investigations of the biogenic degradation of oil, it was shown that bioremediation was accelerated by adding phototrophic partners such as eukaryotic algae and cyanobacteria (SAFONOVA E. TH., DMITRIEVA I. A. and KVITKO K. V. (1999): The interaction of algae with alcanotrophic bacteria in black oil decomposition. In: Resources, Conservation and Recycling 27, p. 193-201.).

SUMMARY OF THE INVENTION

The object of the invention is the development of biologically degradable, free floating porous oil binders in the form of a nonwoven material to accelerate degradation or to remove oil contamination from the surface of the water at sea, in rivers, inland waters as well as storage reservoirs or wastewater treatment plants. In this regard, the shape, dimensions, density and strength of the nonwoven material or oil binder is of particular importance. When using the oil binder, it is not absolutely necessary to recover all of the oil binder which has been deployed because they consist of biogenic materials and are biologically degradable. The oil binder should in particular be quickly at the scene of operations, since the oil spreads at high speed. In addition, the thickness of the oil binder should be as low as possible, since the thickness of the oil slick reduces rapidly and the oil mixes with water, and therefore current absorption techniques thus only have a low efficiency. The novel binder system should also be capable of being deployed under poor weather conditions at sea and on inland waters, and in particular in shallow water regions. In addition, it must have a suitable pourability, since it should also be capable of being deployed from an aircraft. Moreover, the binder must be dimensioned in a manner such that it does not slip through the holes of recovery nets and has sufficient strength and stability. In addition to the biologically degradable oil binder materials, oil-degrading microorganisms which are immobilized on the oil binders, should be a possible component of the material of the invention. Degradation of the oil is particularly important for the binders which cannot be recovered and thus remain in the ecosystem. In this manner, accelerated degradation of the oil can be obtained. For these binders, a long buoyancy period of several days is required.

DETAILED DESCRIPTION OF THE INVENTION

Accordingly, the object of the invention is achieved by means of a porous oil binder in the form of a nonwoven material, consisting of fibres formed from lignocellulosic raw materials. The oil binder has the following features:
  a) the density of the oil binder is 10 to 900 kg/m$^3$, preferably 80 to 300 kg/m$^3$, particularly preferably 220 to 290 kg/m$^3$.
  b) the oil binder is 1 to 25 mm, preferably 3 to 6 mm, particularly preferably 3.5 to 4.5 mm thick.
  c) the large surface of the oil binder has a dimension of 9 to 200 cm$^2$, preferably a dimension of 25 to 100 cm$^2$, particularly preferably in the range 25 to 30 cm$^2$.
  d) the pore fraction of the oil binder is 30% to 96%, preferably 80% to 90%, measured over the entirety of the oil binder.
  e) the bending strength of the oil binder is at least 1.5 N/mm$^2$.

Surprisingly, it has been shown that oil binders which are used with a degree of coverage of at least 10% obtain a clean-up percentage in the range 10% to 100%, preferably 80%. Advantageously, the oil absorption due to the construction of the oil binder is in the range 100 to 700 kg/m$^3$, preferably in the range 400 to 600 kg/m$^3$, wherein after absorbing oil from the environment, an oil binder advantageously has a buoyancy on the surface of the water of at least 3 days, preferably at least 7 days. More advantageously, after absorbing oil from the environment, by producing an overpressure of up to 0.1 bar on the oil binder, the oil binder of the invention does not release any oil. The oil retaining power of the oil binder at an overpressure of 0.1 bar was checked using the LTwS-No 27 guidelines known to the person skilled in the art (Storage and Transport of Water-polluting Substances from the Federal Ministry Advisors on the Environment, Natural Protection and Reactor Safety, issued by the Environmental Agency).

In the context of the invention, "oil" means all of the usual types of oil, such as crude oil, light oil and heavy oil.

The term "density of the oil binder" should be understood to mean the mass of the oil binder in kg with respect to its volume in m$^3$.

The "thickness" of the oil binder refers to the length of the shortest edge of the oil binder.

The "large surface" of the oil binder as used in the context of the invention is the area of the oil binder which comes into contact with the water or oil.

The "pore fraction" of the oil binder describes the volume available for oil absorption with respect to the total volume of the oil binder and was determined in accordance with DIN EN 310, which is familiar to the person skilled in the art. The pore fraction in the context of the invention consists of the voids in the lumen (void in a cell enclosed by the cell wall) of the wood fibres or wood cells and the voids which lie between the wood fibres in the oil binder. The volume of the intermediate fibre voids correlates with the density of the oil binder.

The oil binders have a higher bending strength in order to meet the challenges of deployment and recovery. The bending strength of the oil binder is determined using DIN EN 310, which is known to the person skilled in the art.

The porous oil binder in the form of a nonwoven material may be in the form of flat structures of various shapes, such as polygonal, rectangular, square, round or oval, preferably rectangular.

Preferably, the primarily rectangular structures have a length of side of 10 cm, particularly preferably 5 cm. The length of side in this regard refers to the two longest sides of the rectangular structure.

The invention also concerns a porous oil binder in the form of a nonwoven material, consisting of hydrophobic fibres formed from lignocellulosic raw materials, which are wetted with natural and/or nature-identical additives as hydrophobizing agents and have the following features:
  a) the density of the oil binder is in the range 10 to 900 kg/m$^3$, preferably in the range 80 to 300 kg/m$^3$, particularly preferably in the range 220 to 290 kg/m$^3$.
  b) the thickness of the oil binder is in the range 1 to 25 mm, preferably in the range 3 to 6 mm, particularly preferably in the range 3.5 to 4.5 mm.
  c) the large surface of the oil binder has a dimension of 9 to 200 cm$^2$, preferably a dimension of 25 to 100 cm$^2$, particularly preferably in the range 25 to 30 cm$^2$.
  d) the pore fraction of the oil binder is in the range 30% to 96%, preferably in the range 80% to 90%, measured over the entirety of the oil binder.
  e) the bending strength of the oil binder is at least 1.5 N/mm$^2$.

Preferably, the oil binder comprises hydrophobic fibres formed from lignocellulosic raw materials.

Preferably, the lignocellulosic raw materials consist of wood, grain, flax, rape, rice or cotton straw, coconut, bagasse, bamboo, cork, seaweed, tree bark or mixtures thereof. Seaweed, which occurs on beaches as flotsam, is preferred. Conifers are particularly preferred.

The lignocellulosic raw materials are present in the oil binders in the form of fibres which have a length of 0.1 to 6 mm in the context of the invention. With oil binders formed from coniferous nonwoven materials, the conifer fibres have a length of 0.5 to 4.0 mm.

In a particular embodiment of the invention, the lignocellulosic raw materials are thermally modified. The person skilled in the art will know of various methods for thermally modifying wood fibres. As an example, the wood fibres or the wood are treated prior to milling in the absence of air and/or in a nitrogen atmosphere in an autoclave in a temperature range of 160° C. to 260° C. Advantageously, the wood fibres absorb less water due to the thermal modification.

Preferably, the slenderness ratio of the fibres is 0.5 to 5, particularly preferably 1.0 to 4, more particularly preferably 1.5 to 3, wherein in particular long, slim fibres are advantageous since these have a positive effect on the strength of the oil binder. The term "slenderness ratio" as used in the context of the invention is understood by the person skilled in the art to mean the ratio of the length of the fibres to the diameter of the fibres (Wood Technology Dictionary, $4^{th}$ edition, Leipzig Specialist Publishers, 1990, p 640).

The oil binder of the invention has various pore sizes; advantageously, various types of oils can thus be absorbed.

Furthermore, it is advantageous for the high pore fraction to result in a large specific surface area for the oil binder, whereupon the oil absorption due to adhesion is accelerated.

Preferably, the oil binder may comprise animal-based raw materials in a proportion by weight in the range 5% to 15% by weight, particularly preferably in the range 8% to 12% by weight. Preferably, the animal-based raw materials are wool, feathers or leather, or mixtures thereof.

The combination of lignocellulosic raw materials and animal-based raw materials results in an improved/accelerated oil absorption into the oil binder. Particularly volatile fractions of the oil mixture can be absorbed faster due to the high affinity of the animal-based raw materials.

In a particular embodiment of the invention, the fibres are hydrophobized with natural or nature-identical additives such as paraffins, waxes, synthetic or natural latex, bark extracts, tannins, particularly preferably tannic acid or mixtures thereof. Preferably, the tannins are obtained from wood and/or bark of a quebracho tree and/or an oak.

Surprisingly, it has been shown that the oil absorption in the oil binder in accordance with the invention, because the fibres have been hydrophobized, is much faster than the absorption of water. In moving water, up to 99% by weight of the oil has been absorbed after just 10 to 15 min, while the absorption of water takes several days to weeks. More advantageously, the buoyancy of the oil binder fully loaded with oil is improved by hydrophobizing the surface of the fibre or the oil binder.

Preferably, the fibre surface is wetted with a natural or synthetic binder such as starches, proteins, urea resins, isocyanates or mixtures thereof.

Advantageously, the strength of the oil binder is improved by the binder.

Advantageously, the moisture content of the oil binder of the invention is 5% to 20% by weight, particularly preferably 8% to 15% by weight, measured as the ATRO weight of the fibrous material.

The person skilled in the art will be familiar with the term "ATRO" which describes the dry matter content of the solid after it has been dried to constant weight.

The term "moisture content" is understood by the person skilled in the art to mean the moisture which the oil binder contains when stored in the respective prevailing climate.

Preferably, the surface of the fibre or the oil binder comprises immobilized microorganisms.

Preferably, the microorganisms consist of microorganism communities from alkanotrophic bacteria of the genuses *Rhodococcus*, *Pseudomonas* and *Sphingomonas* as well as phototrophic algae and cyanobacteria from the genuses *Microcoleus, Phormidium, Lyngbya, Oscillatoria* and *Anabaena*.

In a preferred variation, a microorganism community consisting of oil-degrading microorganisms with a phototrophic partner, for example algae or cyanobacteria, is used. These form a biocoenosis, in which the algae produce molecular oxygen for the heterotrophic oil-degrading bacteria and thus prevent oxygen limitation of the bacteria.

Preferably, lyophilized microorganisms accompany the oil binder in accordance with the invention, which microorganisms are suspended just before use in a liquid, preferably water, and then are immobilized on the oil binder.

In accordance with the invention, the buoyant porous oil binders in the form of a nonwoven material for an accelerated degradation or removal of oil contamination from the surface of water in marine environments, rivers, inland waters and also storage reservoirs or wastewater treatment plants are produced by a wet method or by a dry method.

The wet method comprises the following steps:
a) producing fibres from lignocellulosic raw materials by thermal, hydrothermal, mechanical, thermomechanical or chemical digestion methods,
b) isolating and suspending the fibres in a mixing tank with water,
c) adding a hydrophobizing agent and mixing,
d) shaping, dewatering and drying a nonwoven material,
e) shaping the dried nonwoven material, wherein the proportion of fibre in the suspension is 0.5% to 4.5% by weight, particularly preferably 2.5% to 3.5% by weight measured as the total weight of the suspension.

In accordance with the invention, a nonwoven material formed from lignocellulosic raw materials is produced. The lignocellulosic raw materials may be milled into fibres using thermal, hydrothermal, mechanical, thermomechanical or chemical digestion methods such as milling or comminuting methods.

Pre-dewatering of the suspension and shaping of the nonwoven material are carried out by introduction into a screen of a desired size. By pressing, the nonwoven material which is obtained is dewatered further and calibrated to the desired thickness and density and then dried in a dryer. Larger nonwoven materials are then separated into small sheets of the desired size.

Advantageously, the density and bending strength of the oil binder can be adjusted by the size of the screen and the proportion of solid matter in the suspension. The person skilled in the art will be aware of how to select the proportion of solid matter and the screen size in order to obtain a specific density and bending strength.

The dried nonwoven materials are shaped using methods known to the person skilled in the art, for example by cutting or sawing the nonwoven materials into the desired shape.

The dry method comprises the following process steps:
a) producing fibres from lignocellulosic raw materials by thermal, hydrothermal, mechanical, thermomechanical or chemical digestion methods,
b) drying the fibres,
c) sizing and/or wetting the fibres with a natural or synthetic binder and/or a hydrophobizing agent,
d) forming a nonwoven material by pneumatic or manual spreading of the sized and/or wetted fibres,
e) pressing and hardening the nonwoven material.

In accordance with the invention, a nonwoven material is thus produced from lignocellulosic raw materials. The lignocellulosic raw materials are processed into fibres using thermal, hydrothermal, mechanical, thermomechanical or chemical digestion methods.

After digestion, the fibres are dried.

In accordance with a particular embodiment of the invention, natural or nature-identical additives such as paraffins, waxes, synthetic or natural latex, bark extracts, tannins, particularly preferably tannic acid or mixtures thereof are added to the fibres. Preferably, the tannins added are from wood and/or bark from a quebracho tree and/or an oak tree.

Optionally, after drying, natural or synthetic binders such as starches, proteins, urea resins or isocyanates, or mixtures thereof, may be added to the fibres.

Preferably, the natural binders starch and proteins are added in a proportion of 2% to 40% by weight, particularly preferably 5% to 30% by weight with respect to the ATRO weight of the fibrous material.

Preferably, urea resins are added in a proportion of 5% to 18% by weight, particularly preferably 8% to 12% by weight with respect to the ATRO weight of the fibrous material.

Preferably, isocyanates are added in a proportion of 1% to 10% by weight, particularly preferably 2% to 8% by weight with respect to the ATRO weight of the fibrous material.

A nonwoven material is formed by pneumatic or manual spreading of the sized and/or wetted fibres to the desired dimensions.

The nonwoven material is pressed to the desired thickness and hardened.

Larger nonwoven materials are separated into smaller flat structures with various shapes and the desired dimensions, examples of which are polygonal, rectangular, square, round or oval, Rectangular structures are preferred.

Preferably, the rectangular structures have a length of side of 10 cm, particularly preferably 5 cm, in this regard, "length of side" refers to the two longest edges of the rectangular structure.

Preferably, the lignocellulosic raw material used is wood, seaweed, tree bark, grain, flax, rape, rice or cotton straw, coconut fibres, bagasse, bamboo, cork or mixtures thereof. Preferably, seaweed, which occurs as flotsam on beaches, is used. Particularly preferably, coniferous wood is used.

Preferably, animal-based raw materials in a proportion by weight in the range 10% to 15% by weight, particularly preferably in the range 8% to 12% by weight with respect to the total weight of the oil binder, are used. Preferably, wool, feathers or leather, or mixtures thereof, is used as the animal-based raw material.

Preferably, the natural binders such as starches and proteins are added in amounts in the range 2% to 40% by weight, particularly preferably in the range 5% to 30% by weight with respect to the ATRO weight of the fibrous material.

Preferably, oil-degrading microorganisms are immobilized by a spraying and dipping method on the surface of the fibres of the nonwoven material which has been hydrophobized.

Preferably, alkanotrophic bacteria from the genuses *Rhodococcus, Pseudomonas* and *Sphingomonas* as well as phototrophic algae and cyanobacteria from the genuses *Microcoleus, Phormidium, Lyngbya, Oscillatoria* and *Anabaena* are employed.

Immobilisation is carried out during the production or prior to use of the oil binders.

Preferably, for immobilisation, microorganisms which are still lyophilized or in suspension are added during the production of the oil binder and/or prior to use of the oil binder.

The binders obtained act both as a support material for immobilising oil-degrading microorganism communities and also to absorb the oil after deployment. For the accelerated degradation of the oil absorbed by the support material, during production and/or prior to deploying the oil binder material, oil-degrading microorganism communities are immobilized on the surface and/or in the pores of the support material. The microorganisms may be immobilised during or after production of the oil binder, or just before use. On the one hand, oil binders of this type are produced by immersing the nonwoven material in tanks containing microorganisms or by spraying the nonwoven material with oil-degrading microorganisms. On the other hand, in order to ensure a longer storage time (survival), the retained microorganisms are suspended in and applied from an aqueous solution shortly before being used at the scene of the incident.

The oil binders of the invention are provided for the degradation or removal of oil contamination from the surface of the water in seas, rivers, inland waters as well as storage reservoirs or wastewater treatment plants.

By using biogenic, biologically degradable oil binders, the contamination of bodies of water into which the binder is deployed, is reduced or prevented. Inexpensive residual material is used as the support material.

The oil binders can be deployed rapidly both with and without microorganisms using traditional shipping and fishing technology, but also from an aircraft in the region of the oil contamination in the water. In this manner, they can also be used in regions with shallow waters, as well as under difficult weather conditions.

The oil binders are distributed in the region of the oil contamination in the water with a coverage of at least 10%. Surprisingly in this regard, the oil is absorbed to saturation point within a few minutes because of the low density of the oil and the high porosity of the binder while, because of the hydrophobic nature of the fibre, water is absorbed much more slowly, over several days to weeks. In this manner, a clean-up rate for the water surface of more than 80% can be obtained even with a low coverage of only 10%. Absorption of the oil by the oil binder material prevents further contamination of the body of water and the coast and reduces the danger to water birds. In this regard, the oil binder has a buoyant on the water surface which lasts several days.

After absorbing the oil, the loaded oil binder is simply removed from the water using nets and sent for thermal processing.

When loaded oil binders remain in the body of water because of inclement weather conditions or are washed up on inaccessible coasts, the microorganism community can get to work. In a preferred variation, a microorganism community is used which consists of oil-degrading microorganisms with a phototrophic partner, for example algae or cyanobacteria. These form a biocoenosis in which the algae produce molecular oxygen for the heterotrophic oil-degrading bacteria, and thus oxygen limitation of the bacteria is avoided.

Growth is stimulated by contact with the water or oil, the microorganisms colonize the oil film and start to degrade it. Advantageously, microorganisms are used which are suitable for the environmental conditions of the scene of operations. The microorganism community introduced with the oil binder material can accelerate colonization and degradation of the oil contamination by several weeks and months. Degradation of the chemically harmless support material is also carried out with the help of microorganisms which colonise the support material after or during degradation of the toxic oil residues. As a result, the burden on the environment is substantially reduced.

EXAMPLES

The invention will now be explained in more detail with the aid of the following examples.

Example 1a: Production of Oil Binder Material with Latex and Paraffin

Spruce wood chips were processed into fibrous material by thermomechanical milling and a suspension with a solid matter content of 3% by weight was produced therefrom in a mixing tank. The suspension was supplemented with 7% latex milk and 2% paraffin (ATRO fibre solid weight) and it was stirred at 60° C. for approximately 20 min. $Al_2(SO_4)_2$ was added to precipitate it out and the suspension was dewatered using a screen with a vacuum of 0.8 bar. The 4 mm thick nonwoven material was calibrated and dried at 180° C. to a residual moisture content of 8%. The nonwoven material which was produced had a bulk density of 280 $kg/m^3$ and was divided into oil binders with a 5×5 cm length of side. The porosity of the binder was 80% by weight, measured with respect to the entirety of the oil binder (measured with a helium pycnometer in accordance with DIN 51913). The bending strength was 1.98 $N/mm^2$ (in accordance with DIN EN 310).

Example 1b: Production of Oil Binder Material with Natural Latex

Spruce wood fibres were softened in water at a temperature of 50° C. (solids content 3%). Next, 7% of natural latex in a solution was added to the suspension of fibrous material with continuous stirring. $Al_2(SO_4)_3$ was added to the suspension to precipitate it out. Next, the suspension was processed further as described in Example 1a. The bulk density of the oil binder was 265 $kg/m^3$ and the porosity was 81% by weight measured with respect to the entirety of the oil binder. The bending strength was 1.96 $N/mm^2$ (in accordance with DIN EN 310).

Example 1c: Production of Oil Binder Material with Tannin

Spruce wood fibres were softened in water at a temperature of 50° C. (solids content 3%). Next, 5% of quebracho tannin in a solution was added to the suspension of fibrous material with continuous stirring. $Al_2(SO_4)_3$ was added to the suspension to precipitate it out. Next, the suspension was processed further as described in Example 1a and 1b. The bulk density of the oil binder was 279 $kg/m^3$ and the porosity was 80% by weight. The bending strength was 1.97 $N/mm^2$ (in accordance with DIN EN 310).

Example 2: Use of Material as an Oil Binder 50 g of crude oil was measured into individual Petri dishes. 11 g (40 $cm^3$) of the oil binder material from Examples 1a, 1b and 1c were added thereto. After 1 min, in each case the oil binder material had absorbed approximately 27 g of oil (approximately 2.5 times its own weight).

Example 3: Use of Oil Binder in Oil/Water Mixture and Long-Term Buoyancy 1.5 L of water was placed in a container of a shaker. 22.5 g of crude oil (0.3 mm oil layer thickness) and 11 g of oil binder (from Example 1a) with a volume of 40 $cm^3$ was added, corresponding to a coverage of 11%. The container was moved at a frequency of 0.5 Hz. In the first 15 minutes, the increase in weight was measured every 5 min, and thereafter every 10 min. After 10 min, the binder had absorbed an oil/water mixture of 22 g, corresponding to a volume of approximately 600 $kg/m^3$. After a further 80 minutes, a total of 25 g of oil/water mixture had been absorbed. An analysis of the residual water content in the container (separating funnel) showed that 18.41 g of oil and only 7.31 g of water had been absorbed by the binder. This corresponded to an oil uptake of approximately 660 $kg/m^3$ and a clean-up percentage of approximately 85%. The binders floated for a further 14 days in the shaker tank before the test was stopped.

The test was also carried out with oil binders in accordance with Examples 1b and 1c, wherein the oil uptakes were similar to those with the oil binders of Example 1a and the buoyancy was retained for at least 8 days.

What is claimed is:

1. A porous oil sorbent in the form of a nonwoven material, comprising fibres formed from lignocellulosic raw materials, wherein:
    a) the density of the oil sorbent is 80 to 300 $kg/m^3$,
    b) the oil sorbent is 3 to 6 mm thick, wherein thickness of the oil sorbent refers to the length of the shortest edge of the oil sorbent,
    c) the large surface of the oil sorbent has a dimension of 9 to 200 $cm^2$,
    d) the pore fraction of the oil sorbent is 30% to 96%, wherein the pore fraction is determined in accordance with DIN EN 310, and
    e) the bending strength of the oil sorbent is at least 1.5 $N/mm^2$, wherein the bending strength is determined using DIN EN 310.

2. The oil sorbent according to claim 1, wherein the oil sorbent comprises hydrophobized fibres, wherein the fibres are hydrophobized with natural or nature-identical additives, wherein natural or nature-identical additives are paraffins, waxes, synthetic or natural latex, bark extracts, tannins or mixtures thereof.

3. The oil sorbent according to claim 1, wherein the lignocellulosic raw materials are obtained from wood, grain, flax, rape, rice or cotton straw, coconut fibres, bagasse, bamboo, cork, seaweed, tree bark or mixtures thereof.

4. The oil sorbent according to claim 1, wherein the lignocellulosic raw materials contained in the oil sorbent are in the form of partially degraded lignocellulosic raw materials due to thermal modification, wherein the partial degradation due to thermal modification is achieved in the absence of air and/or in a nitrogen atmosphere in an autoclave in a temperature range of 160° C. to 260° C., wherein the lignocellulosic raw materials absorbs less water due to the thermal modification.

5. The oil sorbent according to claim 1, wherein the oil sorbent further comprises animal-based raw materials in a proportion by weight in the range 5% to 15% by weight, wherein animal-based raw materials are wool, feathers or leather, or mixtures thereof.

6. The oil sorbent according to claim 1, wherein the fibre surface further comprises a natural or synthetic binder, wherein the natural or synthetic binder are starches, proteins, urea resins, isocyanates or mixtures thereof.

7. The oil sorbent according to claim 1, wherein the moisture content of the oil sorbent is 5% to 20% by weight, measured as the dry matter content of the fibrous material after it has been dried to constant weight.

8. The oil sorbent according to claim 1, wherein the surface of the fibres or the oil sorbent further comprises immobilized microorganisms, wherein oil-degrading microorganisms are immobilized by a spraying or dipping method on the surface of the fibres of the nonwoven material which has been hydrophobized.

9. The oil sorbent according to claim 8, wherein the microorganism community consists of alkanotrophic bacteria of the genera *Rhodococcus, Pseudomonas* and *Sphingomonas* as well as phototrophic algae and cyanobacteria from the genera *Microcoleus, Phormidium, Lyngbya, Oscillatoria* and *Anabaena*.

10. The oil sorbent according to claim 1 further comprising lyophilised microorganisms or microorganisms in suspension, wherein lyophilised microorganisms or microorganisms in suspension are added during the production of the oil sorbent and/or prior to use of the oil sorbent.

* * * * *